(12) United States Patent
Itu et al.

(10) Patent No.: US 10,463,336 B2
(45) Date of Patent: Nov. 5, 2019

(54) METHOD AND SYSTEM FOR PURELY GEOMETRIC MACHINE LEARNING BASED FRACTIONAL FLOW RESERVE

(71) Applicant: Siemens Healthcare GmbH, Erlangen (DE)

(72) Inventors: Lucian Mihai Itu, Brasov (RO); Puneet Sharma, Monmouth Junction, NJ (US); Saikiran Rapaka, Pennington, NJ (US); Tiziano Passerini, Plansboro, NJ (US); Max Schöbinger, Hirschaid (DE); Chris Schwemmer, Forchheim (DE); Dorin Comaniciu, Princeton Junction, NJ (US); Thomas Redel, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 62 days.

(21) Appl. No.: 15/508,220

(22) PCT Filed: Nov. 16, 2015

(86) PCT No.: PCT/EP2015/076685
§ 371 (c)(1),
(2) Date: Mar. 2, 2017

(87) PCT Pub. No.: WO2016/075331
PCT Pub. Date: May 19, 2016

(65) Prior Publication Data
US 2017/0245821 A1   Aug. 31, 2017

Related U.S. Application Data

(63) Continuation of application No. 14/876,852, filed on Oct. 7, 2015, now Pat. No. 9,918,690, which is a
(Continued)

(51) Int. Cl.
*A61B 6/00* (2006.01)
*G06T 7/00* (2017.01)
(Continued)

(52) U.S. Cl.
CPC .......... *A61B 6/5217* (2013.01); *A61B 5/026* (2013.01); *A61B 5/7267* (2013.01); *A61B 6/032* (2013.01);
(Continued)

(58) Field of Classification Search
CPC .............................. A61B 6/5217; G16H 50/50
See application file for complete search history.

(56) References Cited

U.S. PATENT DOCUMENTS 8,157,742 B2   4/2012   Taylor et al.
10,013,533 B2  7/2018   Iwamura et al.
(Continued)

FOREIGN PATENT DOCUMENTS

| EP | 2949268 | 12/2015 |
|---|---|---|
| JP | 2013233369 A | 11/2013 |
| WO | WO2014042899 A2 | 3/2014 |

OTHER PUBLICATIONS

Kim et al., "Patient-Specific Modeling of Blood Flow and Pressure in Human Coronary Arteries", Annals of Biomedical Engineering, Oct. 2010, vol. 38, Issue 10, pp. 3195-3209.*
(Continued)

*Primary Examiner* — Nay A Maung
*Assistant Examiner* — Jose Torres

(57) ABSTRACT

A method and system for determining hemodynamic indices, such as fractional flow reserve (FFR), for a location of interest in a coronary artery of a patient is disclosed. Medical image data of a patient is received. Patient-specific coronary arterial tree geometry of the patient is extracted from the medical image data. Geometric features are extracted from
(Continued)

the patient-specific coronary arterial tree geometry of the patient. A hemodynamic index, such as FFR, is computed for a location of interest in the patient-specific coronary arterial tree based on the extracted geometric features using a trained machine-learning based surrogate model. The machine-learning based surrogate model is trained based on geometric features extracted from synthetically generated coronary arterial tree geometries.

36 Claims, 9 Drawing Sheets

Related U.S. Application Data continuation of application No. 14/804,609, filed on Jul. 21, 2015, now Pat. No. 9,349,178.

(60) Provisional application No. 62/079,641, filed on Nov. 14, 2014, provisional application No. 62/083,373, filed on Nov. 24, 2014.

(51) Int. Cl.

| | |
|---|---|
| *G06K 9/52* | (2006.01) |
| *G06K 9/62* | (2006.01) |
| *A61B 5/00* | (2006.01) |
| *A61B 5/026* | (2006.01) |
| *A61B 8/06* | (2006.01) |
| *A61B 8/08* | (2006.01) |
| *G06T 7/11* | (2017.01) |
| *A61B 6/03* | (2006.01) |
| *G16H 50/50* | (2018.01) |
| *G16H 50/20* | (2018.01) |
| *G16H 30/20* | (2018.01) |
| *G16H 30/40* | (2018.01) |
| *G16H 20/00* | (2018.01) |
| *A61B 5/02* | (2006.01) |
| *A61B 8/00* | (2006.01) |
| *G06F 19/00* | (2018.01) |

(52) U.S. Cl.
CPC .............. *A61B 6/504* (2013.01); *A61B 6/507* (2013.01); *A61B 8/06* (2013.01); *A61B 8/065* (2013.01); *A61B 8/5223* (2013.01); *G06F 19/00* (2013.01); *G06K 9/52* (2013.01); *G06K 9/6201* (2013.01); *G06K 9/627* (2013.01); *G06K 9/6262* (2013.01); *G06T 7/0012* (2013.01); *G06T 7/11* (2017.01); *G16H 20/00* (2018.01); *G16H 30/20* (2018.01); *G16H 30/40* (2018.01); *G16H 50/20* (2018.01); *G16H 50/50* (2018.01); *H05K 999/99* (2013.01); *A61B 5/02007* (2013.01); *A61B 5/02028* (2013.01); *A61B 5/0263* (2013.01); *A61B 5/743* (2013.01); *A61B 6/469* (2013.01); *A61B 8/469* (2013.01); *A61B 2576/00* (2013.01); *G06F 19/321* (2013.01); *G06T 2200/04* (2013.01); *G06T 2207/10072* (2013.01); *G06T 2207/10076* (2013.01); *G06T 2207/20081* (2013.01); *G06T 2207/30101* (2013.01); *G06T 2207/30104* (2013.01)

(56) References Cited

U.S. PATENT DOCUMENTS

| | | | |
|---|---|---|---|
| 2011/0060576 A1* | 3/2011 | Sharma | ................ G06T 7/0012 703/11 |
| 2012/0041739 A1 | 2/2012 | Taylor | |
| 2013/0246034 A1 | 3/2013 | Sharma et al. | |
| 2013/0132054 A1 | 5/2013 | Sharma et al. | |
| 2014/0073976 A1 | 3/2014 | Fonte et al. | |
| 2014/0249784 A1* | 9/2014 | Sankaran | ............... A61B 6/504 703/2 |
| 2015/0112182 A1 | 4/2015 | Sharma et al. | |
| 2015/0282765 A1* | 10/2015 | Goshen | ................. A61B 6/032 600/408 |
| 2017/0105694 A1* | 4/2017 | Grass | .................... A61B 6/504 |

OTHER PUBLICATIONS

International Search Report dated Jun. 17, 2016 in corresponding International Application No. PCT/EP2015/076685.
Pijls et al., "Measurement of Fractional Flow Reserve to Assess the Functional Severity of Coronary-Artery Stenoses", N Engl J Med, vol. 334, pp. 1703-1708, 1996.
Soudah et al., Validation of numerical flow simulations against in vitro phantom measurements in different type B aortic dissection scenarios, Comput Methods Biomech Biomed Engin. Oct. 25, 2013.
Koo et al., "Diagnosis of Ischemia-Causing Coronary Stenoses by Noninvasive Fractional Flow Reserve Computed from Coronary Computed Tomographic Angiograms", J Am Coll Cardiol, vol. 58, pp. 1989-1997, 2011.
Min et al., Diagnostic Accuracy of Fractional Flow Reserve from Anatomic CT Angiography, JAMA, vol. 308, pp. 1237-1245, 2012.
Renker et al., Comparison of Diagnostic Value of a Novel Noninvasive Coronary Computed Tomography Angiography Method versus Standard Coronary Angiography for Assessing Fractional Flow Reserve, Am J Cardiol, vol. 114, pp. 1303-1308, 2014.
Coenen et al., "Fractional Flow Reserve Computed from Noninvasive CT Angiography Data: Diagnostic Performance of an On-Site Clinician-operated Computational Fluid Dynamics Algorithm", Radiology, online first, 2014.
Morris et al., "Virtual Fractional Flow Reserve from Coronary Angiography: Modeling the Significance of Coronary Lesions", J Am Coll Cardiol Intv, vol. 6, pp. 149-157, 2013.
Japanese Office Action dated Sep. 11, 2018 in corresponding Japanese patent application No. 2017-525590.

* cited by examiner

700

710

720

730

METHOD AND SYSTEM FOR PURELY GEOMETRIC MACHINE LEARNING BASED FRACTIONAL FLOW RESERVE

This application claims the benefit of U.S. Provisional Application No. 62/079,641, filed Nov. 14, 2014, and U.S. Provisional Application No. 62/083,373, filed Nov. 24, 2014, the disclosures of which are incorporated herein by reference in their entirety. This application also claims priority to U.S. application Ser. No. 14/804,609, filed Jul. 21, 2015, and U.S. application Ser. No. 14/876,852, filed Oct. 7, 2015, the disclosures of which are incorporated herein by reference in their entirety.

TECHNICAL FIELD

The present invention relates to non-invasive functional assessment of coronary artery stenosis, and more particularly, to machine learning based non-invasive functional assessment of coronary artery stenosis from medical image data.

BACKGROUND OF THE INVENTION

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel. Measuring the fractional flow reserve (FFR) by inserting a pressure wire into the stenosed vessel has been shown to be a better option for guiding revascularization decisions, since the FFR is more effective in identifying ischemia causing lesions, as compared to invasive angiography. QCA only evaluates the morphological significance if the stenosis and has a number of other limitations. Pressure wire based FFR measurements involve risks associated with the intervention necessary to insert the pressure wire into the vessel, and for a very narrow stenosis, the pressure wire may induce an additional pressure drop.

Recently, mechanistic models have been proposed that use mathematical equations to model the physics of the blood flow in a three-dimensional anatomical model of the coronary vessels of a patient extracted from medical images. Such approaches rely on physics-based mathematical equations to model the physiology at rest and at hyperemia, thereby allowing one to numerically solve the equations on a computer and determine the flow and pressure drop for an individual patient. The most widely used physics-based model is the Navier-Stokes equation, which is a non-linear partial differential equation that is based on principles of mass, momentum, and energy conservation and is used to characterize the flow of blood in the coronary arteries. This is often coupled with mathematical equations that model the physiology of the upstream (heart, aorta) and downstream (myocardium) regions of the anatomy. Depending on the complexity and clinical use case, these methods can be used to incorporate physiological models at various scales. Although various types of physics-based models, boundary conditions, and physiological assumptions have been proposed for blood flow, a common theme of mechanistic models is their use of mathematical equations to model the various physiological interactions explicitly. However, a drawback of such mechanistic models is the high computational cost and complexity of associated with the model preparation and numerical solution of the physics-based equations.

BRIEF SUMMARY OF THE INVENTION

The present disclosure provides methods and systems for machine learning based assessment of hemodynamic indices based purely on geometric features extracted from medical image data. Recently proposed machine learning based methods for estimating patient-specific coronary hemodynamics rely on a large database of patient-specific geometries and physiological measurements, which are used to train a surrogate model against patient-specific computational fluid dynamics (CFD) computations. The features are based on patient-specific measurements (blood pressure, heart rate, geometry, and hematocrit), reduced-order hemodynamic computations, and physiological assumptions. All methods that have been proposed are dependent on the availability of patient-specific measurements in addition to medical imaging for a large number of datasets. Because of this dependency, such methods are not suitable for implementation as a fully automated solution running as a service on an imaging scanner or workstation. No solution is currently available that allows the estimation of fractional flow reserve (FFR) based purely on patient-specific geometric features extracted from medical imaging data.

Embodiments of the present invention calculate coronary artery diagnostic indices, such as FFR and other hemodynamic measurements of interest, using a machine learning data driven approach applied to an exhaustive set of features which are exclusively based on the geometry of the coronary arterial trees. The training phase does not rely on patient-specific data, such as medical images and/or FFR measurements, but instead uses a database of synthetically generated geometries for training a machine learning based surrogate model.

In one embodiment of the present invention, medical image data of a patient is received. Patient-specific coronary arterial tree geometry of the patient is extracted from the medical image data. Geometric features are extracted from the patient-specific coronary arterial tree geometry of the patient. A hemodynamic index is computed for one or more locations of interest in the patient-specific coronary arterial tree based on the extracted geometric features using a trained machine-learning based surrogate model trained based on geometric features extracted from synthetically generated coronary arterial tree geometries.

In another embodiment of the present invention, a plurality of synthetic coronary arterial trees having anomalous regions with varying geometries are generated. Blood flow simulations are performed in the plurality of synthetic coronary arterial trees. Hemodynamic index values are computed at a plurality of locations in each of the plurality of synthetic coronary arterial trees based on the blood flow simulations. Geometric features are extracted from the plurality of synthetic coronary arterial trees. A surrogate model is trained to map the geometric features extracted from the plurality of synthetic coronary arterial trees to the hemodynamic index values computed at the plurality of locations in each of the plurality of synthetic coronary arterial trees using a machine learning algorithm.

These and other advantages of the invention will be apparent to those of ordinary skill in the art by reference to the following detailed description and the accompanying drawings.

DETAILED DESCRIPTION

Figure 1:
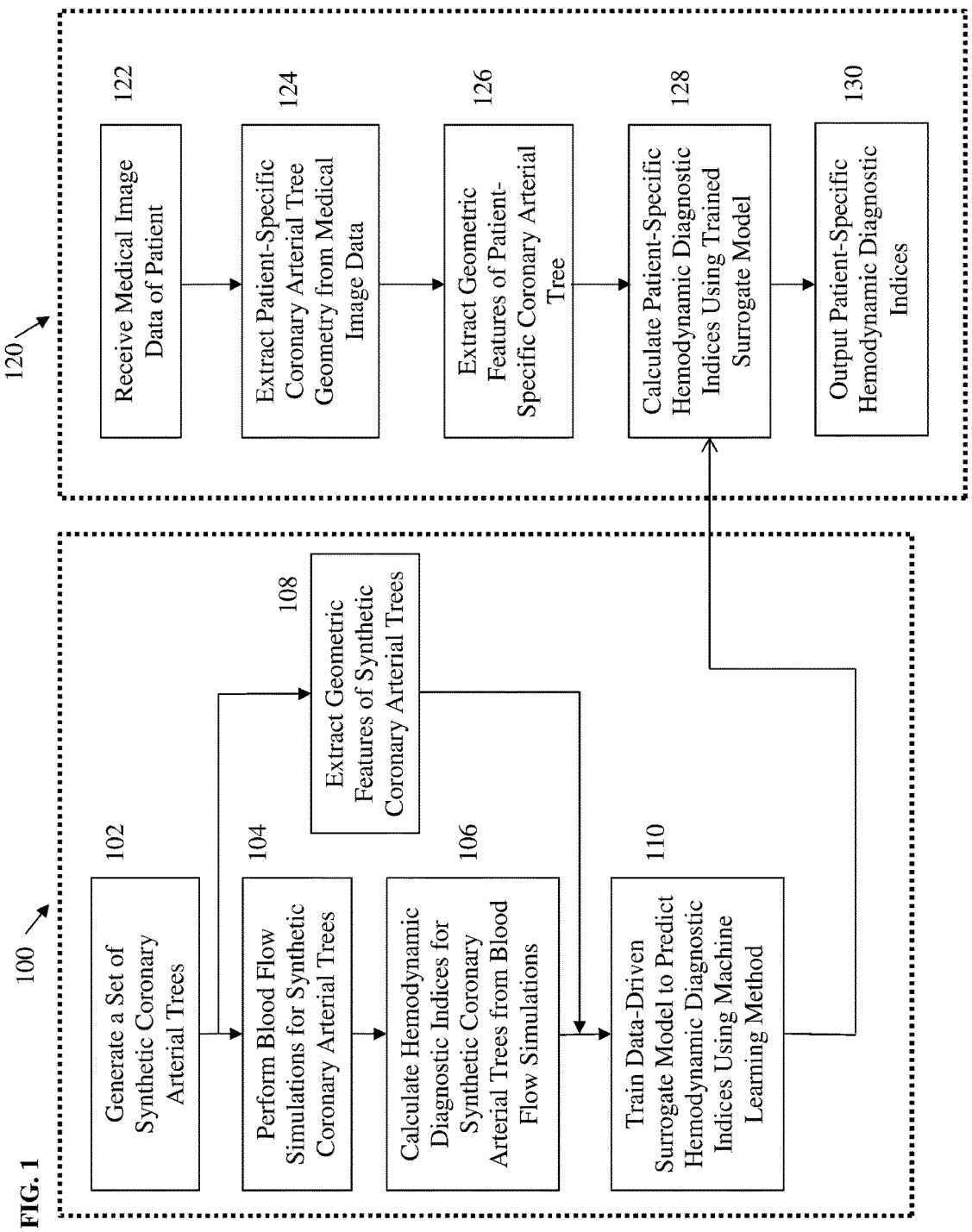
FIG. 1 illustrates a machine learning based method for determining patient-specific hemodynamic indices of coronary arteries from geometric features extracted from medical image data of a patient according to an embodiment of the present invention.

The present invention relates to methods and systems for machine-learning based assessment of hemodynamic indices for coronary artery stenosis, such as fractional flow reserve (FFR). Embodiments of the present invention are described herein to give a visual understanding of the method for assessing coronary artery stenosis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Embodiments of the present invention utilize a data-driven, statistical method to calculate one or more hemodynamic indices based purely on geometric features extracted from medical image data of a patient. Embodiments of the present invention employ machine-learning algorithms to learn the complex mapping between such geometric features and the output quantity of interest (e.g., FFR). Unlike mechanistic model based methods, embodiment of the present invention do not rely on an a priori assumed model describing the relationship between the inputs and the output. Instead, embodiments of the present invention determine the optimal mapping via a statistical approach using machine-learning algorithms to learn the mapping from synthetically generated training data. According to an advantageous embodiment of the present invention, instead of using patient-specific geometries as training data, synthetically generated geometries that are not based on patient-specific data are exclusively used as training data to train data driven surrogate models to predict hemodynamic diagnostic indices. Such synthetic geometries may be generated by varying the shape, severity, location, and number of stenoses, together with the radius and locations of main and side branches in a generic model of a coronary arterial tree. In one possible example of a synthetically generated geometry, a straight tube can be used to represent a coronary artery with a narrowing to represent a stenosis or other anomalies in the coronary artery. Multiple CFD simulations can be performed by varying the synthetic geometry (e.g. minimum radius of the stenosis, entrance angle, exit angle) and varying the inflow or outflow boundary conditions to compute hemodynamic diagnostic indices, such as FFR values. One advantage of using synthetically generated geometries is that it does not require the collection and processing of patient-specific data for completing the training phase, thereby saving both time and cost. Further, there is no limit on the type of synthetic geometries that can be generated, thereby covering a wide spectrum of vessel shapes and topology. Using this approach, the entire training phase can be performed without any patient-specific geometry or image data.

FIG. 1 illustrates a machine learning based method for determining patient-specific hemodynamic indices of coronary arteries from geometric features extracted from medical image data of a patient according to an embodiment of the present invention. The method of FIG. 1 can be applied to compute hemodynamic indices, such as FFR, in order to provide a functional assessment of stenosis regions or other anomalous regions in the coronary arteries. In an advantageous embodiment, the method of FIG. 1 is used to calculate FFR, but the present invention is not limited thereto and the method can be applied to compute other hemodynamic indices as well.

The method of FIG. 1 includes a training phase 100 and a prediction phase 120. The training phase 100 is an offline process, in which one or more data driven surrogate models for predicting hemodynamic indices are trained based synthetically generated coronary artery geometries using a machine learning method. The prediction phase 120 is an online process, whereby one or more patient-specific hemodynamic indices are computed based purely on geometric features extracted from input medical image data of a patient using the trained data driven surrogate model from the training phase 100. Once the training phase 100 is completed, the trained surrogate model is stored, for example in memory or storage of a computer system, and the prediction phase 120 can be repeatedly performed for various patients using the trained surrogate model.

The training phase 100 includes steps 102-110. At step 102, a set of synthetic coronary arterial trees is generated. Instead of using patient-specific geometries as training data, synthetically generated geometries of coronary arterial trees that are not based on patient-specific data are generated and exclusively used as training data. The synthetic coronary arterial trees may be generated by varying the shape, severity, location, and number of stenoses, together with the radius and locations of main and side branches in a generic model of a coronary arterial tree. In an exemplary embodiment, the synthetically generated coronary arterial trees can be implemented using straight tubes to represent coronary arteries with narrowings in the tubes to represent stenoses or other anomalies in the coronary arteries. Other more complex models of coronary artery and stenosis geometry may be used as well. The synthetic coronary arterial trees can include bifurcation stenoses that span the bifurcation of coronary artery branches. The synthetic coronary arterial trees may be generated in silico, i.e., on a computer, using computer models to generate the synthetic coronary arterial trees. In this case a database of synthetic coronary arterial trees having variations in the shape, severity, location, and number of stenoses, as well as varying coronary artery geometries, can be generated and stored on a computer system. It is also possible that the synthetic coronary arterial trees may be generated in vitro using a variety of physical coronary arterial tree models having varying geometries. For example, such physical models can be designed on a computer and generated using 3D printing techniques.

At step 104, blood flow simulations are performed for the synthetic coronary arterial trees. For in silico (computer based) synthetic coronary arterial tree models, computational fluid dynamic (CFD) computations are used to simulate blood flow in the various synthetic coronary arterial trees. Multiple CFD blood flow simulations can be performed for the synthetic coronary arterial trees having varying geometries by varying the inflow and/or outflow boundary conditions. For example, CFD simulations representing resting state blood flow and hyperemic state blood flow may be performed. Well known CFD techniques can be utilized to perform such CFD simulations. Examples of such CFD computations are described in United States Published Patent Application No. 2014/0024932, which is incorporated herein by reference. For in vitro (physical) synthetic coronary arterial tree models, physical flow experiments can be used to perform the blood flow simulations. For example, flow experiments representing resting state and hyperemic state blood flow through the physical synthetic coronary arterial models may be performed.

At step 106, hemodynamic diagnostic indices are calculated for the synthetic coronary arterial trees from the blood flow simulations. In an advantageous embodiment, fractional flow reserve (FFR) can be calculated for multiple sampling points along the coronary artery centerline in each of the synthetic coronary arterial trees. FFR is a functional measure for determining the hemodynamic significance of a coronary stenosis. FFR is defined as the fraction of the flow in the stenosed vessel to the flow in a normal vessel, both of which are determined at maximal hyperemia. FFR can be approximated using pressure data from the blood flow simulations as $$FFR = \frac{P_d - P_v}{P_{A_0} - P_v} = \frac{P_d}{P_{A_0}},$$

where $P_d$ and $P_{A_0}$ are the average distal pressure and aortic pressure, respectively, over the cardiac cycle, and $P_v$ is the venous pressure ($P_v \approx 0$). FFR varies in the range [0, 1], with 0.80 typically being the cut-off value below which a stenosis is deemed hemodynamically significant (i.e., ischemic). In addition to or instead of FFR, other hemodynamic indices, such as pressure-drop, coronary flow reserve (CFR), instantaneous wave-free ratio (IFR), hyperemic stenosis resistance (HSR), basal stenosis resistance (BSR), and index of microcirculatory resistance (IMR), can be calculated at multiple sampling points in each of the synthetic coronary arterial trees. In an advantageous embodiment, wall sheer stress (WSS) is calculated at multiple sampling points in each of the synthetic coronary arterial trees. The WSS values can be used as an index to represent a risk of plaque rupture at a given point. A risk score representing a risk of plaque rupture may also be calculated for each sampling point based on the WSS value.

At step 108, geometric features of the synthetic coronary arterial trees are extracted. As shown in FIG. 1, step 108 may be performed in parallel with steps 104 and 106, but the present invention is not limited thereto. A centerline tree is constructed for each given synthetic coronary arterial tree. The points in the centerline tree are then classified as a start point, ramification points, end points, and interior points. The start point is the first point of the centerline tree corresponding to a coronary ostium. A ramification point is a point where the centerline bifurcates into two or more centerline segments. An end point is a point for which no further downstream centerline point exists. An interior point is a point lying between the start point and a ramification points, two ramification points, or a ramification point and the end point. Each segment of the coronary arterial tree is classified as a root segment, branch segment, or leaf segment. A root segment is a segment delimited by a start point and a ramification point. A branch segment is a segment delimited by two ramification points. A leaf segment is a segment delimited by a ramification point and an end point. Each coronary artery segment (root/branch/leaf) is then divided into one or more segments characterized as anomalous (non-healthy) or non-anomalous (healthy) segments. An anomalous (non-healthy) segment is a segment which has an abnormal luminal narrowing or dilation. A non-anomalous (healthy) is a segment which has no abnormal luminal narrowing or dilation.

The features extracted for the sampling points of each synthetic coronary arterial tree are entirely based on geometry. In an advantageous embodiment, such features include an ischemic weight w and an ischemic contribution score s. The ischemic weight w is an ischemic weight value associated with each coronary artery segment (i.e., root, interior, or leaf segment). The ischemic contribution score s is computed for specific finite length segments of coronary artery geometry comprising one or more branches. The ischemic contribution score is computed from a series of geometric properties and from ischemic weights of the particular segments.

Figure 2:
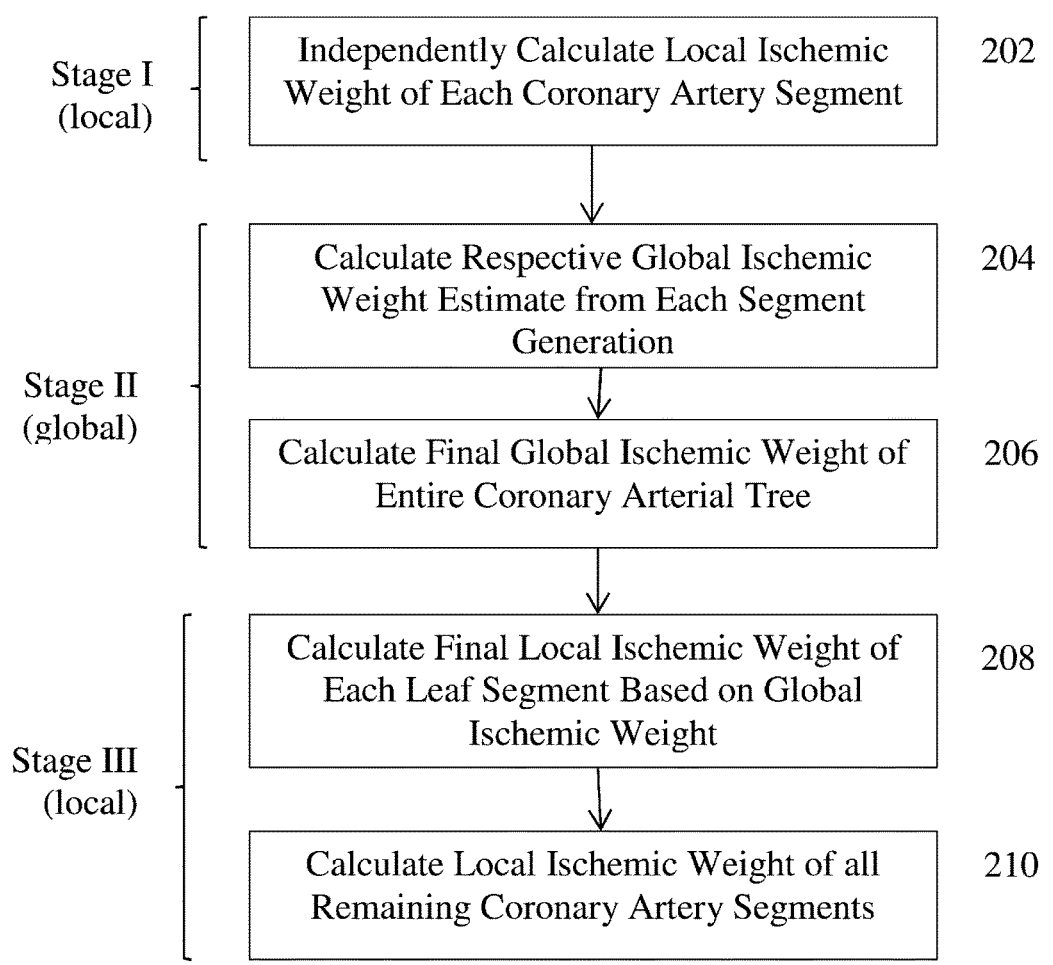
FIG. 2 illustrates a method for calculating ischemic weights for a coronary arterial tree according to an embodiment of the present invention.

Regarding the ischemic weight, w, it can be assumed that the ischemic weight value of each coronary segment corresponds to the ischemic weight values of all downstream segments. FIG. 2 illustrates a method for calculating ischemic weights for a coronary arterial tree according to an embodiment of the present invention. The method of FIG. 2 can be used to calculate the ischemic weights for the synthetic coronary arterial trees in step 108 of the training phase 100 of FIG. 1 and to calculate ischemic weights for the patient-specific coronary arterial tree in step 126 of the prediction phase 120 of FIG. 1. To compute the ischemic weights, the method of FIG. 2 uses a three stage local-to-global-to local approach. In a first local stage (Stage I of FIG. 2), a separate ischemic weight is computed for each coronary artery segment. As these ischemic values are computed independently, there is no guarantee that the original assumption holds (e.g., the sum of the ischemic weights of two daughter segments is not necessarily equal to the ischemic weight of the parent segment). Accordingly, in a global stage (Stage II of FIG. 2), a global ischemic weight of the entire coronary arterial tree is computed by averaging the weight of different segments in different generations. In a final local stage (Stage III of FIG. 2), the global ischemic weight is distributed to the individual segments in a way that satisfies the original assumption.

Referring to FIG. 2, stage I is implemented by step 202. At step 202, a local ischemic weight is independently calculated for each coronary artery segment. In particular, for each root segment, branch segment, and leaf segment, the local ischemic weight value can be calculated using:

$$w = k_1 \cdot r_{ref}^n, \qquad (1)$$

where $r_{ref}$ is the reference radius of the segment, $k_1$ is a proportionality constant, and n is a power coefficient. In exemplary implementations, the power coefficient n may take values between 2 (for large arteries) and 3 (for small arteries). Since, regularly, the radius along the centerline of a segment, r(x), is continuously varying, a mathematical operator $f_1$ is applied to calculate the reference radius value $r_{ref}$ for each coronary artery segment:

$$r_{ref} = f_1(r(x)). \qquad (2)$$

where r(x) is the radius of the coronary artery segment and x is a position along the centerline of the coronary artery segment. In a possible implementation, the operator $f_1$ can calculate an average value of healthy radiuses along the entire length of the segment or a part of the segment. When used herein, "healthy radiuses" refer to radiuses of healthy (non-anomalous) portions of a segment. In another possible implementation, the operator $f_1$ can calculate an average value of the healthy radiuses along the entire length of the segment or a part of the segment, excluding the largest x % and the smallest y % of the healthy radius values. In another possible implementation, the operator $f_1$ can calculate the maximum or minimum value of healthy radiuses along the entire length of the segment or a part of the segment. It is to be understood that the operator $f_1$ is not necessarily limited to these operations and other possible calculations can also be used to estimate the reference radius of a segment.

Figure 3:
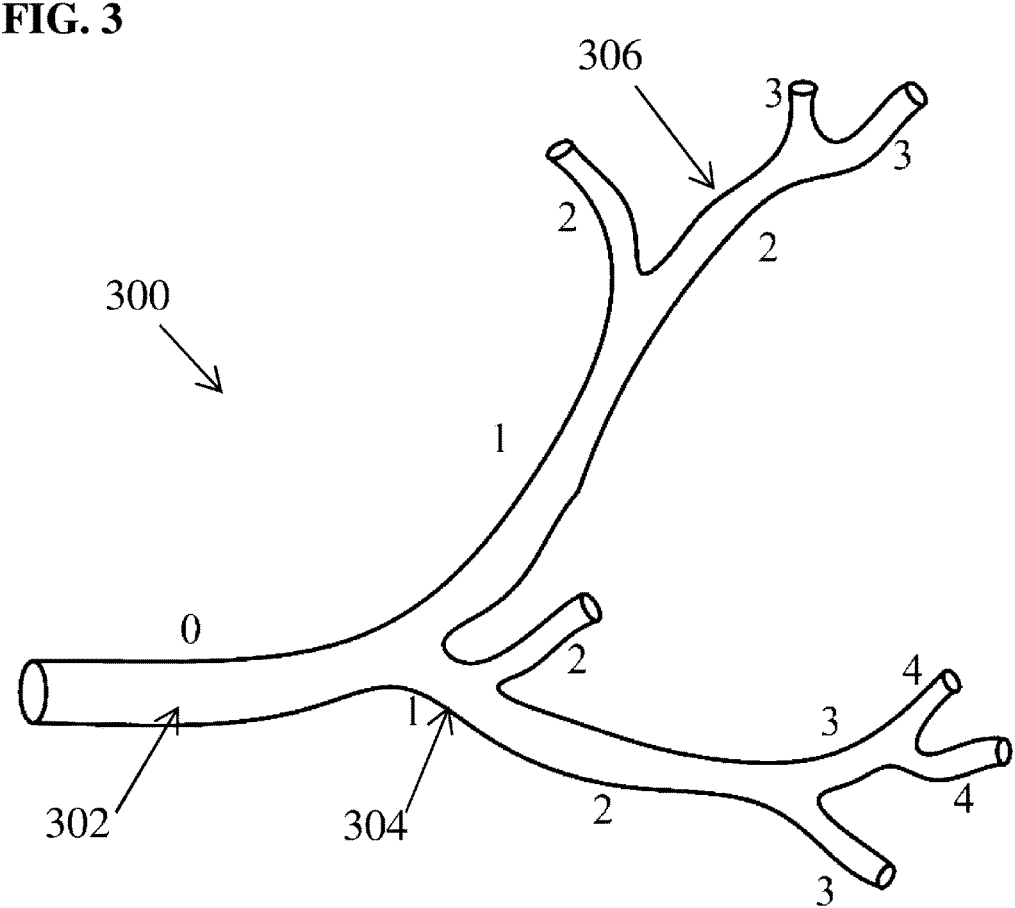
FIG. 3 illustrates an example of a coronary artery tree with a generation number assigned to each coronary artery segment.

In stage II of FIG. 2, a global ischemic weight value for the entire coronary arterial tree (left or right coronary arterial tree) is computed based on the local ischemic weights calculated in stage I (step 202). Stage II is implemented by steps 204 and 206. At step 204, a respective global ischemic weight for the coronary arterial tree is calculated from each generation of segments based on the local ischemic weights of the segments calculated in step 202. FIG. 3 illustrates an example of a coronary artery tree 300 with a generation number assigned to each coronary artery segment. As shown in FIG. 3, the root segment 302 of the coronary artery tree 300 has a generation number 0, and at each bifurcation the generation number increases by one. A separate estimate for the global ischemic weight of the coronary artery tree can be estimated from segments of each generation number. The global ischemic weight estimate for the coronary tree calculated using the branches with the generation number g is calculated as follows. Before estimating the global ischemic weight from generation number g, a confidence value $c_i$ is assigned to each segment representing a confidence in the correctness of the estimated reference radius for that segment. The segments can be weighted based on the length of the segment and/or the percentage of the branch that is diseased (anomalous). Accordingly, short segments, such as the bottom segment 304 with the generation number equal to 1 in FIG. 3, or entirely diseased segments, such as the diffusely diseased segment 306 with the generation number equal to 2 in FIG. 3, are assigned low confidence values, while long segments without radius irregularities are assigned large confidence values. The confidence values may be normalized to range between 0 (minimum confidence) and 1 (maximum confidence). A global ischemic weight for the entire coronary artery tree is then estimated based on the segments from generation g using the local ischemic weights $w_i$ calculated for the segments from generation g and the confidence values $c_i$ assigned to those segments using a mathematical operator $f_2$:

$$(w_{global})_g = f_2(c_i, w_i), \qquad (3)$$

where the index i refers to all segments from generation g and all leaf segments with a generation number smaller than g. For example, $(w_{global})_g$ for each generation g can be calculated as:

$$(w_{global})_g = \Sigma_i c_i \cdot w_i. \qquad (4)$$

A plurality of global ischemic weight estimates are calculated by calculating respective a global ischemic weight estimate based on segments from each generation g between $g_{min}$ and $g_{max}$. In an advantageous implementation, the minimum generation level $g_{min}$ can be 0, but can also be larger than 0 if the root node is very short. The maximum generation level can be set to determine how many generations are used in calculating the total rest flow rate of the coronary artery tree. In advantageous implementations, the value for the maximum generation level $g_{max}$ may be set to 3 or 4. Branches of higher generations become increasingly smaller, which makes an accurate estimation of the reference radius and corresponding local ischemic weights using the higher generation branches more difficult. Furthermore, when the coronary arterial tree geometry is reconstructed from medical image data (in the prediction phase 120), small side branches may not be accounted for in the model. Hence, the higher the generation number, the higher the number of side branches not been considered will be, leading to a larger error in the flow rate estimation.

Returning to FIG. 2, at step 206, a final global ischemic weight of the entire coronary arterial tree is calculated from the global ischemic weight estimates calculated from the various generations of segments. To improve accuracy of the final global ischemic weight of the coronary arterial tree, the global ischemic weight estimates calculated from multiple different segment generations are used to calculate the final total global ischemic weight value. In particular, the global ischemic weight estimates calculated from each generation g between $g_{min}$ and $g_{max}$ are used to calculate the final global ischemic weight value for the coronary arterial tree. Before estimating the final global ischemic weight of the entire coronary arterial tree, a confidence value $d_i$ is assigned to each generation number, representing a confidence in the correctness of the global ischemic weight estimate calculated from the segments with the corresponding generation number. Low generation numbers can be assigned large weights, while large generation numbers can be assigned low weights as smaller side branches may be missed in patient-specific coronary arterial tree geometry (in the prediction phase 120) as the generation number increases. For example, the confidence values $d_j$ can have an inverse relationship to the generation number. The confidence values $d_j$ may be normalized to range between 0 (minimum confidence) and 1 (maximum confidence). The final global ischemic weight value is estimated as a function of the global ischemic weight estimates for the various generations $(w_{global})_j$ and the corresponding confidence values $d_j$ assigned to the generations using a mathematical operator $f_3$:

$$w_{global} = f_3(d_j, (w_{global})_j), \qquad (5)$$

where the index j refers to a generation between $g_{min}$ and $g_{max}$. For example, the global ischemic weight for the coronary arterial tree can be calculated as a weighted mean:

$$w_{global} = \frac{\Sigma_j d_j \cdot (w_{global})_j}{\Sigma_j d_j}. \qquad (5)$$

In stage III of FIG. 2, final local ischemic weight values for the segments of the coronary arterial tree are computed by distributing the global ischemic weight calculated in stage II to the individual coronary artery segments. Stage III is implemented by steps 208 and 210. At step 208, the final local ischemic weight is calculated for each of the leaf segments of the coronary arterial tree based on the global ischemic weight of the coronary arterial tree. The local ischemic weights for the leaf segments of the coronary arterial tree can be calculated by distributing the global ischemic weight of the coronary arterial tree over all of the leaf segments based on the reference ratios or the initial ischemic weight values individually calculated for leaf segments. In particular, the local ischemic weight for the each of coronary leaf segments can be calculated as:

$$w_k = \frac{(r_{ref})_k^n}{\Sigma_k (r_{ref})_k^n} w_{global}, \qquad (6)$$

where k refers to the leaf segments of the coronary arterial tree.

At step 210, the final local ischemic weight values of the remaining segments of the coronary arterial tree are calculated based on the final local ischemic weights of the leaf segments. The final ischemic weight values of the branch segments and the root segment are calculated as a sum of the downstream leaf segments. That is, for each remaining coronary artery segment (root segment and branch segments), the final local ischemic weight is calculated as:

$$w_l = \Sigma_{k_l} w_{k_l}, \qquad (7)$$

where l refers to a current coronary artery segment and $k_l$ refers to all leaf segments lying downstream from the current segment l.

Figure 4:
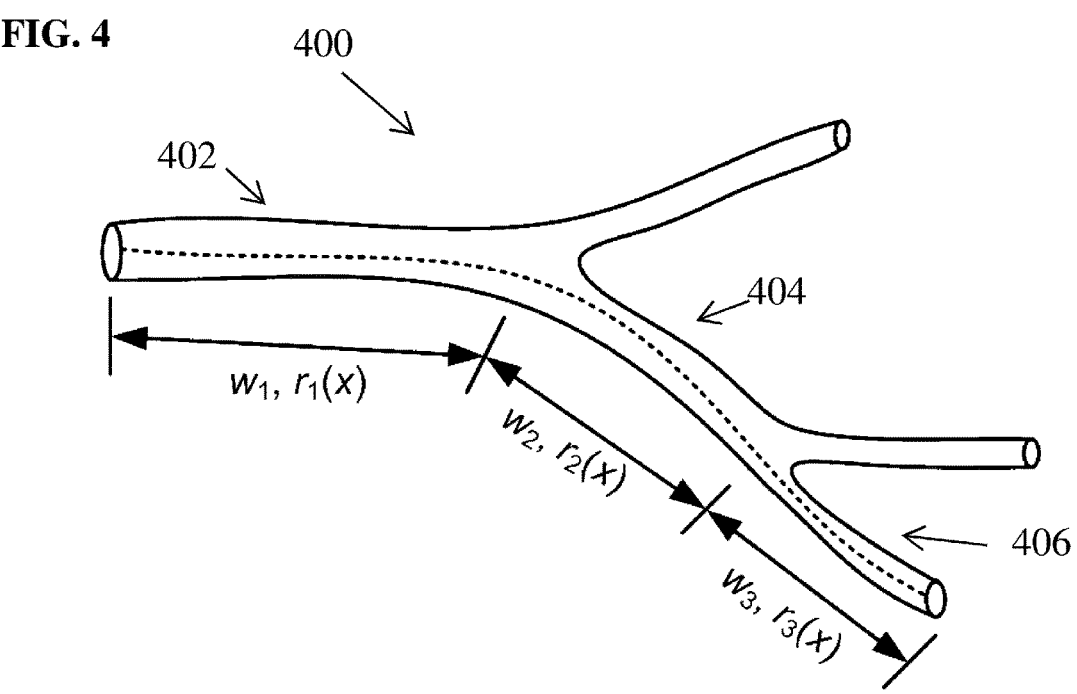
FIG. 4 illustrates calculation of an ischemic contribution score for a non-anomalous length of coronary artery.

The ischemic contribution score can be computed for any non-zero finite length coronary artery segment or segments which may or may not contain ramifications. The ischemic contribution score is computed differently for non-anomalous (healthy) and anomalous (non-healthy) segments. Non-anomalous segments will have low ischemic contribution scores. FIG. 4 illustrates calculation of an ischemic contribution score for a non-anomalous length of coronary artery. For a non-anomalous length of coronary artery, such as the multi-segment coronary artery length 400 shown in FIG. 4, the ischemic contribution score can be calculated using the formula:

$$s = k_2 \int_0^L \frac{w(x)}{r(x)^n} dx, \qquad (9)$$

where L is the total length of the segment(s), $k_2$ is a proportionality constant, n is a power coefficient, r(x) is the radius which varies along the centerline, and w(x) is the ischemic weight, which can vary along the centerline if ramifications are present, as shown in FIG. 4. As shown in FIG. 4, the length 400 of coronary artery has ramifications and is thus divided into three segments 402, 404, and 406. Segment 402 has an ischemic weight of $w_1$ (calculated using the method of FIG. 2) and a radius $r_1(x)$ that may vary along the centerline. Segment 404 as an ischemic weight of $w_2$ and a radius $r_2(x)$ that may vary along its centerline. Segment 406 as an ischemic weight of $w_3$ and a radius $r_3(x)$ that may vary along its centerline. The ischemic contribution score of the entire multi-segment length 400 of coronary artery can be computed using equation (9).

Figure 5:
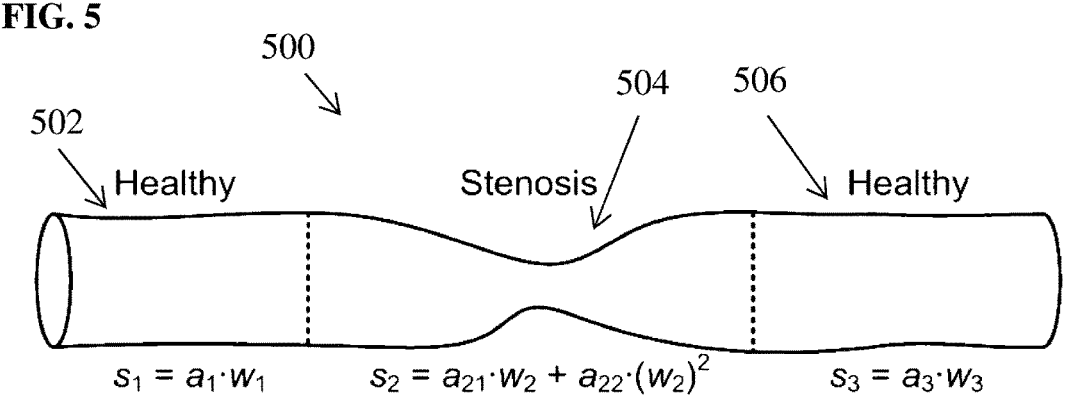
FIG. 5 illustrates calculation of an ischemic contribution score for a partially diseased vessel segment.

Anomalous (non-healthy) segments (e.g., stenosis segments) have higher ischemic contribution scores, whereas the higher the severity of the lesion (e.g., stenosis), the higher the ischemic contribution score will be. The calculation of the ischemic contribution score is described herein for the non-healthy stenosed segments, but may be similarly applied for other types of pathologies (e.g., aneurysm) as well. FIG. 5 illustrates calculation of an ischemic contribution score for a partially diseased vessel segment. As shown in FIG. 5, a coronary artery segment 500 two healthy segments 502 and 506 and a stenosis segment 504. For a stenosis that stretches along a single root, branch, or leaf segment, such as stenosis 504 of FIG. 5, the ischemic contribution score is calculated using the formula:

$$s = f_4(r(x)) w_l + f_5(r(x)) w_l^2, \qquad (10)$$

where $f_4$ and $f_5$ are mathematical operators applied to the longitudinally varying radius of the stenosis segment and $w_l$ is the ischemic weight of the segment. Various mathematical operators can be used for $f_4$ and $f_5$. In an exemplary implementation, $f_4$ uses mean of the radius along the stenosis, such that $f_4(r(x)) = k_3 \cdot \overline{r(x)}$, where $\overline{r(x)}$ is the mean of the radius over the stenosis segment and $k_3$ is a proportionality constant. In another exemplary implementation, $f_4$ uses integral of the inverse of the radius, such that $$f_4(r(x)) = k_4 \cdot \int_0^L \frac{1}{r(x)^n} dx,$$

wherein $k_4$ is a proportionality constant, L is the length of the stenosis segment, and n is a power coefficient. $f_5$ may be calculated using the radius at the top and bottom of the stenosis. In one exemplary implementation, $f_5$ is calculated as $$f_5(r(x)) = k_5 \cdot \left( \frac{1}{r_{bottom}^2} - \frac{1}{r_{top}^2} \right),$$

where $k_5$ is a proportionality constant, $r_{top}$ refers to the healthy radius at the proximal end of the stenosis segment, and $r_{bottom}$ refers to the healthy radius at the distal end of the stenosis segment. In another exemplary implementation, $f_5$ is calculated as $$f_5(r(x)) = k_6 \cdot \left( \frac{1}{r_{min}} - \frac{1}{r_{bottom}} \right)^2,$$

where $k_5$ is a proportionality constant, $r_{min}$ refers to the minimum radius of the stenosis segment, and $r_{bottom}$ refers to the healthy radius at the distal end of the stenosis segment. In addition to the ischemic score computed using equation (10), the two components of equation (10) may also be separately used as training features for training the surrogate model, and each component may also be divided into subcomponents which can then be used as features as well.

As shown in FIG. 5, separate ischemic contribution scores $s_1$, $s_2$, and $s_3$ are calculated for healthy segment 502, stenosis segment 504, and healthy segment 506, respectively. For the healthy segments 502 and 506, the ischemic scores are respectively calculated as $s_1 = a_1 \cdot w_1$ and $s_3 = a_3 \cdot w_3$, where $w_1$ and $w_3$ are the ischemic weights of segments 502 and 506, respectively, and $a_1$ and $a_3$ refer to the result of applying a mathematical operator to the longitudinally varying radius of segments 502 and 506, respectively, such as the mathematical operator of $$k_2 \cdot \int_0^L \frac{1}{r(x)^n} dx,$$

which is applied in equation (9). For the stenosis segment 504, the ischemic score is calculated as $s_2 = a_{21} \cdot w_2 + a_{22} \cdot (w_2)^2$, where $w_2$ is the ischemic weight of segment 504 and $a_{21}$ and $a_{22}$ refer to the respective results of applying mathematical operators $f_4$ and $f_5$ to the longitudinally varying radius of the stenosis segment 504 using equation (10).

Figure 6:
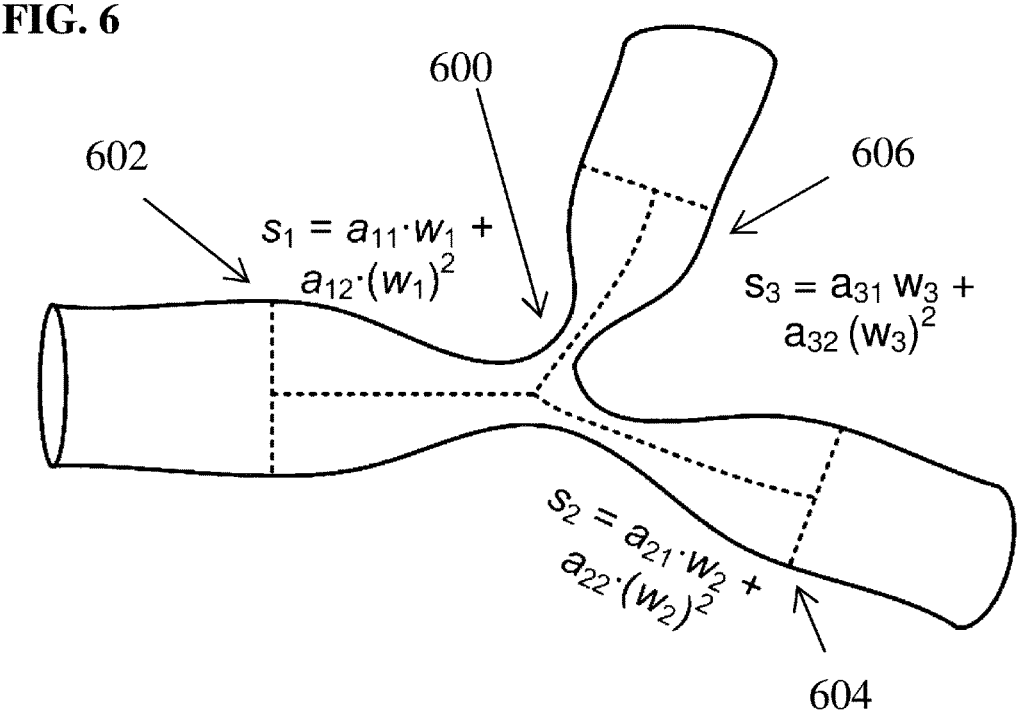
FIG. 6 illustrates calculation of ischemic contribution scores for a bifurcation stenosis.

In the case of bifurcation stenoses, i.e., stenoses which stretch over a bifurcation along multiple root, branch, or leaf segments, a separate ischemic contribution score is computed using equation (10) for each root, branch, or leaf segment of the stenosis pertaining to either the parent or the daughter segments. FIG. 6 illustrates calculation of ischemic contribution scores for a bifurcation stenosis. As shown in FIG. 6, a stenosis 600 stretches over a bifurcation along coronary artery segments 602, 604, and 606. Separate ischemic contribution scores $s_1$, $s_2$, and $s_3$ are calculated using equation (10) for the respective portions of the stenosis 600 in segments 602, 604, and 606, respectively. The ischemic contribution score $s_1$ for the portion of the stenosis in segment 602 is calculated as $s_1 = a_{11} \cdot w_1 + a_{12} \cdot (w_1)^2$, where $w_1$ is the ischemic weight of segment 602 and $a_{11}$ and $a_{12}$ refer to the respective results of applying mathematical operators $f_4$ and $f_5$ to the longitudinally varying radius of the stenosis in segment 602 using equation (10). The ischemic contribution score $s_2$ for the portion of the stenosis in segment 604 is calculated as $s_2 = a_{21} \cdot w_2 + a_{22} \cdot (w_2)^2$, where $w_2$ is the ischemic weight of segment 604 and $a_{21}$ and $a_{22}$ refer to the respective results of applying mathematical operators $f_4$ and $f_5$ to the longitudinally varying radius of the stenosis in segment 602 using equation (10). The ischemic contribution score $s_3$ for the portion of the stenosis in segment 606 is calculated as $s_3 = a_{31} \cdot w_3 + a_{32} \cdot (w_3)^2$, where $w_3$ is the ischemic weight of segment 606 and $a_{31}$ and $a_{32}$ refer to the respective results of applying mathematical operators $f_4$ and $f_5$ to the longitudinally varying radius of the stenosis in segment 606 using equation (10).

Based on the ischemic contribution scores of individual segments, multiple features representing cumulative ischemic contribution scores can be computed at any location in the coronary arterial tree. Cumulative ischemic contribution scores of multiple segments can be calculated by adding the ischemic contribution scores of the segments together. For a current location in a coronary arterial tree (e.g., a sampling point in a synthetically generated coronary arterial tree), multiple ischemic contribution score features can be calculated including one or more of the following features:

Cumulative ischemic contribution score computed from all segments lying between the root segment and the current location;

Cumulative ischemic contribution score computed from the non-anomalous (healthy) segments lying between the root segment and the current location;

Cumulative ischemic contribution score computed from the anomalous (non-healthy/pathological/stenosis) segments lying between the root segment and the current location;

Cumulative ischemic contribution score computed from all segments lying between the current location and a leaf segment. The path from the current location to the leaf segment can for example be determined by choosing at each ramification the path along the main daughter segment, as determined from a combination of properties, such reference radius, total length downstream, total number of generations downstream, etc.;

Cumulative ischemic contribution score computed from the non-anomalous (healthy) segments lying between the current location and a leaf segment; and/or Cumulative ischemic contribution score computed from the anomalous (non-healthy/pathological/stenosis) segments lying between the current location and a leaf segment.

In addition to the ischemic weight and ischemic contribution score features described above, other geometric features can be extracted from the coronary arterial trees as well. For example, for each stenosis (anomalous segment) in the coronary arterial tree the following geometric features are extracted: proximal radius of the stenosis, distal radius of the stenosis, minimum radius of the stenosis, percentage diameter of the stenosis computed from the proximal radius and minimum radius, percentage diameter of the stenosis computed from the distal radius and the minimum radius, total stenosis length, entrance length of the stenosis (length from start of stenosis to location with minimum radius), exit length of the stenosis (length from location with minimum radius to end of stenosis), and minimum radius length (length of the stenosis in the region of minimum radius—a tolerance can be used for detecting the region around the location with minimum radius). Furthermore, various combinations obtained through algebraic, integration, or derivation operations applied to proximal, distal, and minimum radii of the stenosis can also be used as features. The ischemic contribution scores and the other geometric features described above can be computed separately for all pathologic segments lying upstream and downstream from the current location. Then they can be ordered based on a chosen criterion (ischemic contribution score or some other feature) and used as an ordered list of features.

Returning to FIG. 1, at step 110, a data-driven surrogate model is trained based on the extracted geometric features to predict the hemodynamic diagnostic indices using a machine learning method. Once the hemodynamic indices for various sampling points in the synthetic coronary arterial trees are determined from the blood flow simulations and the geometric features are extracted from the synthetic coronary arterial trees, a surrogate model that provides mapping between the input geometric features and the hemodynamic indices is determined by using a machine learning algorithm. The type of machine learning algorithm used to train the surrogate model may be a supervised, semi-supervised, transductive, or reinforcement based learning algorithm. For example, machine learning algorithms, such as regression algorithms (linear, non-linear, or logistic), decision trees or graphs, association rule learning, artificial neural networks, support vector machines, inductive logic programming, Bayesian networks, instance-based learning, manifold learning, sub-space learning, deep learning, dictionary learning, etc., may be used to train the machine-learning based surrogate model. According to an advantageous embodiment, the trained surrogate model is a learned data-driven surrogate model that combines the extracted features with various learned weights. A separate surrogate model may be trained for each hemodynamic index or measurement of interest. For example, separate surrogate models can be trained to compute FFR, WSS, and other hemodynamic indices such as IFR, HSR, BSR, and IMR.

In the prediction phase 120 (steps 122-130) of FIG. 1, the trained surrogate model (or models) is used to predict a patient-specific hemodynamic index (such as FFR) based purely on geometric features extracted from medical image data of a patient. In the prediction phase 120, at step 122, medical image data of a patient is received. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D, or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient. In an advantageous embodiment, 3D coronary CT angiography (CTA) images are acquired on a CT scanner. The CTA images ensure that the coronary vasculature, including the vessel(s) that contain the stenosis, is adequately imaged using a contrast agent that is injected into the patient.

At step 124, patient-specific coronary arterial tree geometry is extracted from the medical image data of the patient. The patient-specific coronary arterial tree geometry can be patient-specific geometric measurements for a full coronary artery tree of the patient or patient-specific geometric measurements for any portion less than the full coronary artery tree of the patient. In a possible implementation, the patient-specific coronary arterial tree geometry can be patient-specific anatomical measurements of only a left coronary artery (LCA) tree or a right coronary artery (RCA) tree.

Figure 7:
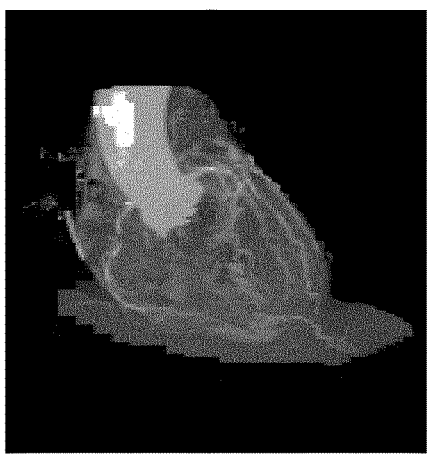
FIG. 7 illustrates exemplary results for generating a patient-specific anatomical model of the coronary artery tree.
Figure 7:
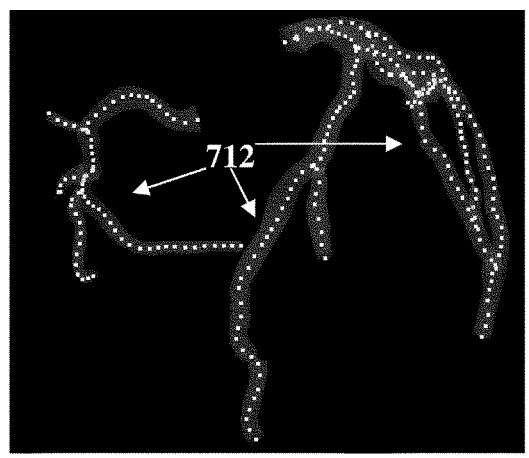
Figure 7:
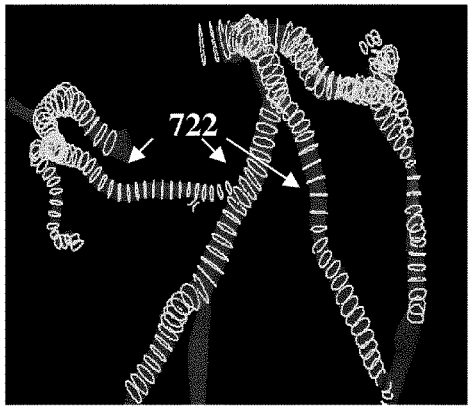
Figure 7:
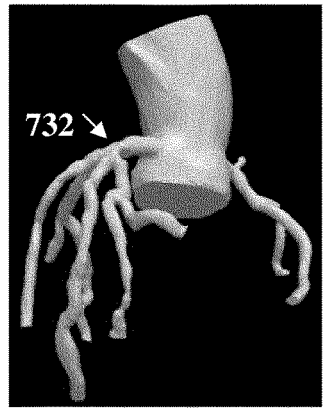

In an advantageous embodiment, the patient-specific coronary arterial tree geometry is extracted by segmenting a patient-specific anatomical model of the coronary arterial tree from the medical image data, but the present invention is not limited thereto. The patient-specific anatomical model may be a patient-specific anatomical model of any portion of the full coronary artery tree of the patient. In order to generate the patient-specific anatomical model of the coronary artery tree, the coronary arteries can be segmented in the 3D medical image data using an automated coronary artery centerline extraction algorithm. For example, the coronary arteries can be segmented in a CT volume using the method described United States Published Patent Application No. 2010/0067760, which is incorporated herein by reference. Once a coronary artery centerline tree is extracted, cross-section contours can be generated at each point of the centerline tree. The cross-section contour at each centerline point gives a corresponding cross-section area measurement at that point in the coronary artery. A geometric surface model is then generated for the segmented coronary arteries. For example, methods for anatomical modeling of the coronary arteries are described in U.S. Pat. Nos. 7,860,290 and 7,953,266, both of which are incorporated herein by reference. FIG. 7 illustrates exemplary results for generating a patient-specific anatomical model of the coronary vessel tree. Image 700 of FIG. 7 shows coronary CTA data. Image 710 shows a centerline tree 712 extracted from the CTA data. Image 720 shows a cross-section contours 722 extracted at each point of the centerline tree 712. Image 730 shows a 3D surface mesh 732 of the coronary arteries, the aortic root, and the proximal part of the aorta. It is to be understood that the anatomical model of the coronary tree of the patient can be output and displayed, for example on a display screen of the computer system.

In an alternative embodiment, the patient-specific coronary arterial tree geometry can be extracted by extracting geometric measurements of the coronary arterial tree directly from the image data without segmenting a full patient-specific anatomical model of the coronary arteries. For example, a coronary artery centerline can be detected in the image data as described above, and then a radius of the coronary artery can be automatically detected at each centerline point. These geometric measurements can then be used to calculate the geometric features in step 126.

Anomalous (e.g., stenosis) regions of the coronary arteries are identified. For example, stenosis regions can be automatically segmented in the medical image data or in the patient-specific anatomical model of the coronary artery tree. In one embodiment, a machine-learning based method can be used to automatically detect stenosis regions in the medical image data. Such a method for automatic detection of coronary artery stenosis is described in United States Published Patent Application No. 2011/0224542, which is incorporated herein by reference. In another embodiment, stenosis regions may be automatically detected from the extracted coronary artery centerline and radius values of the centerline points by detecting centerline points in which the radius decreases and the increases again beyond a tolerance value. In another embodiment, user input identifying the stenosis regions can be received, for example, by a user clicking on stenosis regions of the medical image data or segmented coronary artery tree on a display device of a computer system using a user input device.

Returning to FIG. 1, at step 126, geometric features are extracted from the patient-specific coronary arterial tree. In particular, the features described above in connection with step 108 of the training phase 100 are extracted for the patient-specific coronary arterial tree. Such features include the ischemic weights of the various segments of the patient-specific coronary arterial tree, the ischemic contribution scores (including multiple cumulative ischemic contribution scores), and geometric measurements of the anomalous/stenosis regions in the patient-specific coronary arterial tree. The calculation of such features purely from the geometry of the patient-specific coronary arterial tree is performed as described above in connection with step 108.

At step 128, patient-specific hemodynamic diagnostic indices are computed based on the geometric features using the trained surrogate model. The trained surrogate model is a data driven model trained exclusively from synthetic (non-patient-specific) training data. The trained surrogate model inputs the extracted geometric features and calculates hemodynamic indices (such as FFR) for particular locations in the patient-specific coronary arterial tree based on the extracted geometric features. The trained surrogate model computes the patient-specific hemodynamic indices based purely on the geometric features extracted from the medical image data and does not consider any other features from patient-specific physiological measurements, such as blood pressure or heart rate. In order to compute a hemodynamic index for a particular location in the patient-specific coronary arterial tree, the trained surrogate model can be trained to consider geometric features (e.g., ischemic contribution scores, ischemic weights, geometric measurements) extracted upstream and downstream of the current location, in addition to features extracted at that location. In one embodiment, the trained surrogate model can automatically compute the hemodynamic indices for a plurality of locations without any user input. For example, the trained surrogate model can automatically compute hemodynamic indices for all centerline points of the patient-specific coronary artery centerline, a plurality of locations automatically sampled from the centerline points of the patient-specific coronary artery centerline (e.g., skip every n centerline points), or at locations corresponding to each of the stenosis regions in the patient-specific coronary artery centerlines. In another embodiment, the user may input a location, for example by clicking on the location on a display device of computer system, and the trained surrogate model can compute the patient-specific hemodynamic index (e.g., FFR, WSS, etc.) at the input location in real time in response to receiving the user input. Multiple trained surrogate models may be used to compute multiple hemodynamic indices at locations in the patient-specific coronary arterial model. For example, separate trained surrogate models may be used for computing FFR, WSS, and other hemodynamic indices such as IFR, HSR, BSR, and IMR.

At step 130, the patient-specific hemodynamic indices computed by the trained surrogate model are output. For example, values for such indices may be displayed on a display device. When a hemodynamic index is computed by the trained surrogate model in response to a user input identifying a location, the value for the hemodynamic index can be displayed in real time to the user. In a possible implementation, the values for a hemodynamic index for one or more locations can be displayed by overlaying those values at their corresponding locations on a displayed image of the patient-specific coronary arterial centerline or on the displayed medical image data of the patient. When hemodynamic indices for multiple locations are automatically computed using the trained surrogate model an image showing the locations and the corresponding values for the hemodynamic indices may be automatically displayed. In a possible implementation a color-coded visualization of the patient-specific coronary arterial centerline may be displayed in which locations on the coronary arterial centerline are color coded based on a severity of the hemodynamic index (e.g., FFR). In an embodiment in which WSS is the hemodynamic index, high wall sheer stress values can correspond to locations with high risk of plaque rupture, and a map showing locations with high risk of plaque rupture can be displayed.

The method of FIG. 1 can be used to provide real-time FFR computation in the prediction phase 120. As the trained surrogate model is trained exclusively on synthetically generated coronary arterial trees, the method of FIG. 1 does not need matched CTA and FFR data for training. The synthetic training data can cover all types of pathologies and anomalous cases, including various combinations of coronary artery pathology types (e.g., single segment stenosis, bifurcation stenosis with either one or all parent and daughter branches being affected, diffuse disease, aneurysms, serial lesions, collateral circulation, etc.) and various severities. The method of FIG. 1 can also be expanded to address other diseases (e.g., aortic stenosis, cerebral stenosis, peripheral stenosis) by appending the training data with synthetic cases characterizing the geometric scale of these vessels.

Figure 8:
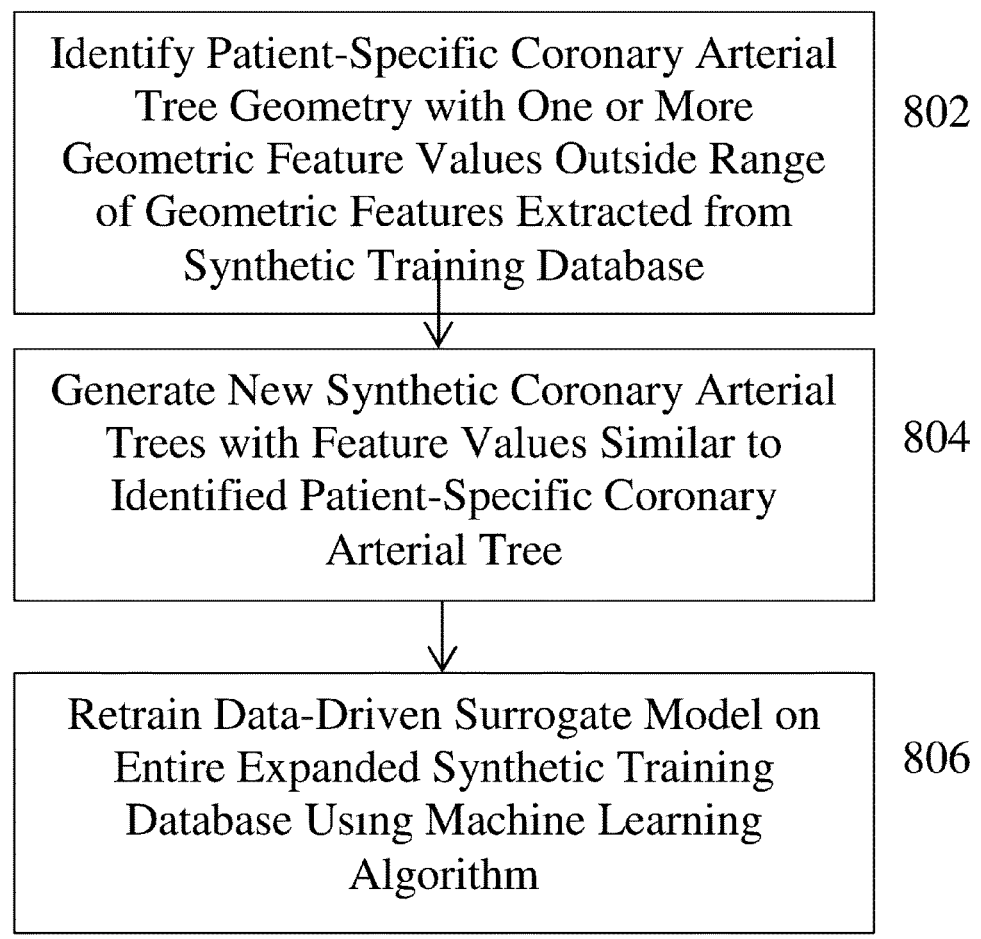
FIG. 8 illustrates a method for expanding the synthetic training database and updating the trained surrogate model according to an embodiment of the present invention.

According to an advantageous embodiment, since synthetic training data is used to train the data-driven surrogate model, the training database can be vastly expanded at little additional cost. Although a very large number of synthetic cases can be generated for training the machine-learning based surrogate model, these cases may not cover all patient-specific cases. Hence, when applying the trained surrogate model to predict results for patient-specific data in the prediction phase, some features computed for the patient-specific data may have values which are outside of the range of values covered by the synthetic database. FIG. 8 illustrates a method for expanding the synthetic training database and updating the trained surrogate model according to an embodiment of the present invention. The method of FIG. 8 can be applied to enrich the database of synthetic cases so as to increase the range of feature values covered by the synthetic database, and thus to also cover feature values computed for the patient-specific data that are outside the range of the feature values covered by the synthetic training database. At step 802, a patient-specific coronary arterial centerline geometry with one or more geometric features outside a range of the features extracted from the synthetic training database is identified. In particular, in the prediction phase (120 of FIG. 1) when the geometric features (e.g., ischemic weights, ischemic contribution scores, geometric measurements of stenoses) are extracted for a patient-specific coronary arterial tree (step 126 of FIG. 1), the geometric features are compared to a range of features extracted from all of the synthetic coronary arterial centerlines in the synthetic training database to determine if any of the features from the patient-specific coronary arterial tree fall outside the range of the corresponding features in the synthetic training database. At step 804, new synthetic coronary arterial trees are generated having feature values similar to the features of the identified patient-specific coronary arterial tree. For example, multiple new synthetic coronary arterial trees may be generated to span feature values between the previous range of features in the synthetic training database and the new feature outside of the previous range. At step 806, the data-driven surrogate model is re-trained on the entire expanded synthetic training database using a machine learning algorithm. This results in an updated ad improved trained surrogate model that can then be used to perform the prediction phase to predict the hemodynamic indices.

The real-time performance of the method of FIG. 1, as well as the fact that it relies on a synthetically generated training database, which can be expanded on-demand and virtually without limit, makes this method advantageous for therapy planning applications. One of the therapies widely used for treating arterial stenosis is stenting, i.e. the placement of a metal or polymer stent in the artery to open up the lumen, and hence facilitate the flow of blood. When dealing with coronary stenosis, the stenting therapy is referred to as PCI—Percutaneous Coronary Intervention. This is an example of an intervention that aims at restoring the healthy function of the arterial tree by altering its geometry, and as such can be naturally described based on the geometric features used by our method. For example, any system for the virtual placement of the stent in an anatomical geometrical model extracted from medical images can be coupled with the machine-learning based surrogate model. The trained surrogate model can compute all hemodynamic quantities of interest that would result from each candidate therapy option, therefore predicting the outcome of PCI, and allowing the planning of an optimal PCI procedure. A particularly relevant example is the use of this method to plan therapy in multi-vessel disease scenarios, in terms of which stenosis to stent to achieve the optimal outcome.

According to an advantageous embodiment, instead of performing a virtual placement of the stent in the anatomical model extracted from medical images, the features used by the machine learning algorithm may be directly adapted to account for the effect of the treatment. Thus, first the features are determined for the original patient-specific anatomical model, next they are adapted, either automatically or by using information input by the user (for example, the user may specify different levels for the success of the treatment: partially successful treatment of the stenosis region, fully successful treatment of the stenosis region, etc.), and finally the machine learning based trained surrogate model is applied to compute the post-treatment hemodynamic metric. For example, the features may be directly adapted to account for the effect of the treatment by adjusting the ischemic contribution scores. In a possible implementation, the ischemic contribution scores may be adapted by using different formulations for the mathematical operators $f_4$ and $f_5$, which would lead to smaller ischemic contribution scores. In terms of the machine learning algorithm based trained surrogate model, either the same trained surrogate model used for the pre-treatment predictions may be used, or a different machine learning trained surrogate model may be trained on synthetic cases representative for post-treatment geometries and used for predicting post-treatment hemodynamic indices.

In a possible extension to the method of FIG. 1, the hemodynamic index (e.g., FFR) estimated at a location upstream from a current location using the trained surrogate model can also be used as a feature for computing the hemodynamic index at the current location by the trained surrogate model. In another possible extension to the method of FIG. 1, the ischemic contribution scores can include information about known associations between geometry features and pathology severity, for instance based on literature evidence (e.g. for coronaries, proximity to a bifurcation (plaque stability); this also applies to different diseases, e.g. for aneurysms: aspect ratio; etc.).

According to an advantageous embodiment of the present invention, the sensitivity of the hemodynamic index with respect to one or more of the geometric features may be determined by using the trained machine learning based surrogate model by varying the features in a certain range. It is also possible that the sensitivity of the hemodynamic index with respect to one or more of the geometric features may be predicted using a different trained surrogate model trained using a different machine learning algorithm. The sensitivity of the hemodynamic diagnostic index with respect to one or more of the geometric features is computed and visualized for the patient-specific data during the prediction phase by varying the one or more geometric features within a predetermined range and computing the hemodynamic index with the trained surrogate model. This information can be used to inform the user and/or the machine learning algorithm of which geometric features are more relevant to the accuracy of the prediction of the hemodynamic index.

Figure 9:
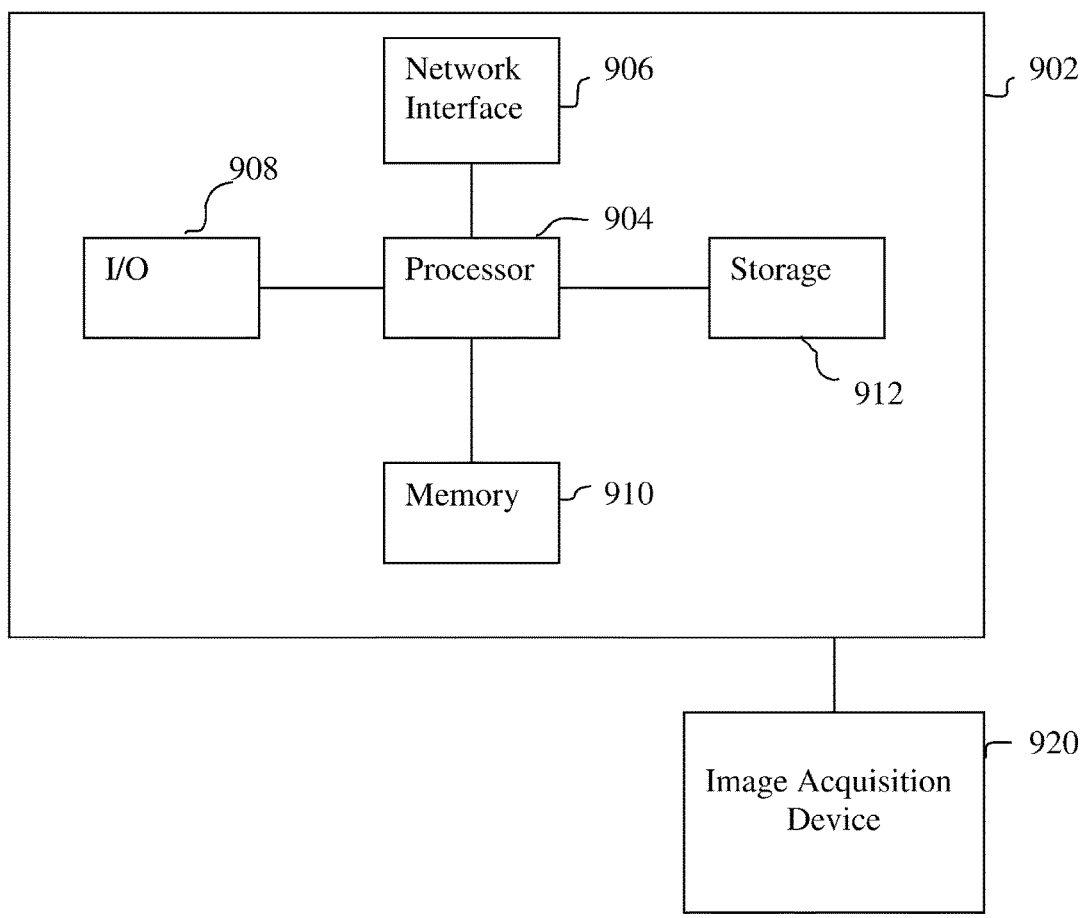
FIG. 9 is a high-level block diagram of a computer capable of implementing the present invention.

The above-described methods for training a machine-learning based surrogate model data and determining hemodynamic indices based purely on geometric features using a trained machine-learning based surrogate model can be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 1, 2, and 8 may be defined by the computer program instructions stored in the memory 910 and/or storage 912 and controlled by the processor 904 executing the computer program instructions. An image acquisition device 920, such as a CT scanning device, MR scanning device, Ultrasound device, etc., can be connected to the computer 902 to input image data to the computer 902. It is possible to implement the image acquisition device 920 and the computer 902 as one device. It is also possible that the image acquisition device 920 and the computer 902 communicate wirelessly through a network. In a possible implementation, the computer 902 may be located remotely from the image acquisition device and may perform one or more of the method steps as a cloud-based or server-based service. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for determining a hemodynamic index for one or more locations of interest in coronary arteries of a patient, comprising:
   receiving medical image data of the patient;
   extracting patient-specific coronary arterial tree geometry of the patient from the medical image data;
   extracting geometric features from the patient-specific coronary arterial tree geometry of the patient; and
   computing a hemodynamic index for one or more locations of interest in the patient-specific coronary arterial tree using a trained machine-learning based surrogate model and based purely on the extracted geometric features without considering features from patient-specific physiological measurements, the trained machine-learning based surrogate model trained based on geometric features extracted from synthetically generated coronary arterial tree geometries.

2. The method of claim 1, wherein the trained machine-learning based surrogate model is trained on geometric features extracted exclusively from synthetically generated non-patient-specific coronary arterial tree geometries.

3. The method of claim 1, wherein extracting geometric features from the patient-specific coronary arterial tree geometry of the patient comprises:

calculating ischemic weights for coronary artery segments based on the patient-specific coronary arterial tree geometry; and calculating ischemic contribution scores for coronary artery segments based on the ischemic weights.

4. The method of claim 3, wherein calculating ischemic weights for coronary artery segments based on the patient-specific coronary arterial tree geometry comprises:

individually calculating initial local ischemic weights for each of a plurality of coronary artery segments based on a respective reference radius value calculated for each of the plurality of coronary artery segments;

calculating a global ischemic weight for the patient-specific coronary arterial tree based on the initial local ischemic weights for the plurality of coronary artery segments; and calculating final local ischemic weights for each of the plurality of coronary artery segments by distributing the global ischemic weight over the plurality coronary artery segments.

5. The method of claim 4, wherein calculating a global ischemic weight for the patient-specific coronary arterial tree based on the initial local ischemic weights for the plurality of coronary artery segments comprises:

calculating a plurality of global ischemic weight estimates for the patient-specific coronary arterial tree, wherein each of the plurality of global ischemic weight estimates is calculated from initial local ischemic weights of coronary artery segments from a respective one of a plurality of generations of coronary artery segments; and calculating the global ischemic weight of the patient-specific coronary arterial tree based on the plurality of global ischemic weight estimates.

6. The method of claim 5, wherein calculating a plurality of global ischemic weight estimates for the patient-specific coronary arterial tree, wherein each of the plurality of global ischemic weight estimates is calculated from initial local ischemic weights of coronary artery segments from a respective one of a plurality of generations of coronary artery segments comprises, for each of the plurality of generations of coronary artery segments:

assigning a weight to each of the coronary artery segments in that generation of coronary artery segments and leaf coronary artery segments with a generation number smaller than that generation of coronary artery segments; and calculating the estimate for the global ischemic weight of the patient-specific coronary arterial tree as a function of the initial ischemic weights of coronary artery segments in that generation of coronary artery segments and the leaf coronary artery segments with a generation number smaller than that generation of coronary artery segments and the weights assigned to each of the coronary artery segments in that generation of branches and the leaf coronary artery segments with a generation number smaller than that generation of coronary artery segments.

7. The method of claim 5, wherein calculating the global ischemic weight of the patient-specific coronary arterial tree based on the plurality of global ischemic weight estimates comprises:

calculating the global ischemic weight of the patient-specific coronary arterial tree as a function of the plurality of global ischemic weight estimates and weights corresponding to the plurality of generations of coronary artery segments.

8. The method of claim 4, wherein calculating final local ischemic weights for each of the plurality of coronary artery segments by distributing the global ischemic weight over the plurality coronary artery segments comprises:

calculating the final local ischemic weights of a plurality of leaf coronary artery segments by distributing the global ischemic weight over the leaf coronary artery segments based on the initial local ischemic weights of the leaf coronary artery segments; and calculating the final local ischemic weight for each remaining one of the plurality of coronary artery segments as a sum of the final local ischemic weights of leaf segments downstream from that coronary artery segment.

9. The method of claim 3, wherein calculating ischemic contribution scores for coronary artery segments based on the ischemic weights comprises:

dividing coronary artery segments into non-anomalous portions and anomalous portions;

calculating the ischemic contribution scores for each non-anomalous portion based on a spatially varying radius of the non-anomalous portion and the ischemic weight of the coronary artery segment in which the non-anomalous portion is located; and calculating ischemic contribution scores for each anomalous portion based on a first product of the ischemic weight of the coronary artery segment in which the anomalous portion is location and a first mathematical operator applied to a spatially varying radius of the anomalous portion and a second product of a squared ischemic weight of the coronary artery segment in which the anomalous portion is located and a second mathematical operator applied to the spatially varying radius of the anomalous portion.

10. The method of claim 9, wherein extracting geometric features from the patient-specific coronary arterial tree geometry of the patient further comprises:

for each of the one or more locations of interest, calculating one or more of a cumulative ischemic contribution score from all coronary segments lying between a root segment and a current location, a cumulative ischemic contribution score from the non-anomalous portions of coronary artery segments lying between the root segment and the current location, a cumulative ischemic contribution score from the anomalous portions of coronary artery segments lying between the root segment and the current location, a cumulative ischemic contribution score from all coronary artery segments lying between the current location and a leaf segment, a cumulative ischemic contribution score from the non-anomalous portions of coronary artery segments lying between the current location and a leaf segment, or a cumulative ischemic contribution score from the anomalous portions of coronary artery segments lying between the current location and a leaf segment.

11. The method of claim 3, wherein extracting geometric features from the patient-specific coronary arterial tree geometry of the patient further comprises:

extracting a plurality of geometric measurements for one or more stenosis regions in the patient-specific coronary arterial tree geometry of the patient.

12. The method of claim 1, wherein the one or more locations of interest correspond to one or more stenosis locations, and computing a hemodynamic index for one or more locations of interest in the patient-specific coronary arterial tree using a trained machine-learning based surrogate model and based purely on the extracted geometric features without considering features from patient-specific physiological measurements comprises:

automatically computing the hemodynamic index for the one or more stenosis locations in the patient-specific coronary arterial tree using the trained machine-learning based surrogate model and based purely on the extracted geometric features without considering features from patient-specific physiological measurements.

13. The method of claim 1, wherein computing a hemodynamic index for one or more locations of interest in the patient-specific coronary arterial tree using a trained machine-learning based surrogate model and based purely on the extracted geometric features without considering features from patient-specific physiological measurements comprises:

computing the hemodynamic index for the one or more locations of interest in the patient-specific coronary arterial tree in response to a user input identifying the one or more locations of interest.

14. The method of claim 1, wherein the hemodynamic index is fractional flow reserve (FFR).

15. The method of claim 1, wherein the hemodynamic index is wall stress.

16. The method of claim 15, further comprising determining a risk of plaque rupture at the one or more locations of interest based on the wall stress computed for the one or more locations of interest using the trained machine-learning based surrogate model.

17. The method of claim 1, wherein computing a hemodynamic index for one or more locations of interest in the patient-specific coronary arterial tree using a trained machine-learning based surrogate model and based purely on the extracted geometric features without considering features from patient-specific physiological measurements comprises:

computing a plurality of hemodynamic indices for each of the one or more locations of interest in the patient-specific coronary arterial tree using a respective one of a plurality of trained machine-learning based surrogate models and based purely on the extracted geometric features without considering features from patient-specific physiological measurements.

18. The method of claim 1, further comprising:
determining that at least one of the geometric features extracted from the patient-specific coronary arterial tree geometry is outside a range of corresponding features in a synthetic training database including the synthetically generated coronary arterial tree geometries used to train the machine-learning based surrogate model;
generating one or more new synthetic coronary arterial tree geometries based on the features extracted from the patient-specific coronary arterial tree geometry to expand the synthetic training database; and
re-training the machine-learning based surrogate model based on geometric features extracted from the synthetic coronary arterial tree geometries in the expanded synthetic training database using a machine learning algorithm.

19. A method of training a data-driven surrogate model for predicting a hemodynamic index purely from geometric features of a coronary arterial tree, comprising:

generating a plurality of synthetic coronary arterial trees having anomalous regions with varying geometries;

performing blood flow simulations in the plurality of synthetic coronary arterial trees;

computing hemodynamic index values at a plurality of locations in each of the plurality of synthetic coronary arterial trees based on the blood flow simulations;

extracting geometric features from the plurality of synthetic coronary arterial trees; and training a surrogate model to map the geometric features extracted from the plurality of synthetic coronary arterial trees to the hemodynamic index values computed at the plurality of locations in each of the plurality of synthetic coronary arterial trees using a machine learning algorithm and based purely on the extracted geometric features without considering features from patient-specific physiological measurements.

20. An apparatus for determining a hemodynamic index for one or more locations of interest in coronary arteries of a patient, comprising:

a processor; and a memory to store computer program instructions, the computer program instructions when executed on the processor cause the processor to perform operations comprising:

receiving medical image data of the patient;

extracting patient-specific coronary arterial tree geometry of the patient from the medical image data;

extracting geometric features from the patient-specific coronary arterial tree geometry of the patient; and computing a hemodynamic index for one or more locations of interest in the patient-specific coronary arterial tree using a trained machine-learning based surrogate model and based purely on the extracted geometric features without considering features from patient-specific physiological measurements, the trained machine-learning based surrogate model trained based on geometric features extracted from synthetically generated coronary arterial tree geometries.

21. The apparatus of claim 20, wherein the trained machine-learning based surrogate model is trained on geometric features extracted exclusively from synthetically generated non-patient-specific coronary arterial tree geometries.

22. The apparatus of claim 20, wherein extracting geometric features from the patient-specific coronary arterial tree geometry of the patient comprises:

calculating ischemic weights for coronary artery segments based on the patient-specific coronary arterial tree geometry; and calculating ischemic contribution scores for coronary artery segments based on the ischemic weights.

23. The apparatus of claim 22, wherein extracting geometric features from the patient-specific coronary arterial tree geometry of the patient further comprises:

extracting a plurality geometric measurements for one or more stenosis regions in the patient-specific coronary arterial tree geometry of the patient.

24. The apparatus of claim 20, wherein the hemodynamic index is fractional flow reserve (FFR).

25. The apparatus of claim 20, wherein the hemodynamic index is wall stress.

26. The apparatus of claim 20, wherein computing a hemodynamic index for one or more locations of interest in the patient-specific coronary arterial tree using a trained machine-learning based surrogate model and based purely on the extracted geometric features without considering features from patient-specific physiological measurements comprises:

computing a plurality of hemodynamic indices for each of the one or more locations of interest in the patient-specific coronary arterial tree using a respective one of a plurality of trained machine-learning based surrogate models and based purely on the extracted geometric features without considering features from patient-specific physiological measurements.

27. A non-transitory computer readable medium storing computer program instructions for determining a hemodynamic index for one or more locations of interest in coronary arteries of a patient, the computer program instructions defining when executed by a processor cause the processor to perform operations comprising:
receiving medical image data of the patient;
extracting patient-specific coronary arterial tree geometry of the patient from the medical image data;
extracting geometric features from the patient-specific coronary arterial tree geometry of the patient; and
computing a hemodynamic index for one or more locations of interest in the patient-specific coronary arterial tree using a trained machine-learning based surrogate model and based purely on the extracted geometric features without considering features from patient-specific physiological measurements, the trained machine-learning based surrogate model trained based on geometric features extracted from synthetically generated coronary arterial tree geometries.

28. The non-transitory computer readable medium of claim 27, wherein the trained machine-learning based surrogate model is trained on geometric features extracted exclusively from synthetically generated non-patient-specific coronary arterial tree geometries.

29. The non-transitory computer readable medium of claim 27, wherein extracting geometric features from the patient-specific coronary arterial tree geometry of the patient comprises:
calculating ischemic weights for coronary artery segments based on the patient-specific coronary arterial tree geometry; and
calculating ischemic contribution scores for coronary artery segments based on the ischemic weights.

30. The non-transitory computer readable medium of claim 29, wherein calculating ischemic weights for coronary artery segments based on the patient-specific coronary arterial tree geometry comprises:
individually calculating initial local ischemic weights for each of a plurality of coronary artery segments based on a respective reference radius value calculated for each of the plurality of coronary artery segments;
calculating a global ischemic weight for the patient-specific coronary arterial tree based on the initial local ischemic weights for the plurality of coronary artery segments; and
calculating final local ischemic weights for each of the plurality of coronary artery segments by distributing the global ischemic weight over the plurality coronary artery segments.

31. The non-transitory computer readable medium of claim 29, wherein calculating ischemic contribution scores for coronary artery segments based on the ischemic weights comprises:
dividing coronary artery segments into non-anomalous portions and anomalous portions;
calculating the ischemic contribution scores for each non-anomalous portion based on a spatially varying radius of the non-anomalous portion and the ischemic weight of the coronary artery segment in which the non-anomalous portion is located; and
calculating ischemic contribution scores for each anomalous portion based on a first product of the ischemic weight of the coronary artery segment in which the anomalous portion is location and a first mathematical operator applied to a spatially varying radius of the anomalous portion and a second product of a squared ischemic weight of the coronary artery segment in which the anomalous portion is located and a second mathematical operator applied to the spatially varying radius of the anomalous portion.

32. The non-transitory computer readable medium of claim 29, wherein extracting geometric features from the patient-specific coronary arterial tree geometry of the patient further comprises:
for each of the one or more locations of interest, calculating one or more of a cumulative ischemic contribution score from all coronary segments lying between a root segment and a current location, a cumulative ischemic contribution score from the non-anomalous portions of coronary artery segments lying between the root segment and the current location, a cumulative ischemic contribution score from the anomalous portions of coronary artery segments lying between the root segment and the current location, a cumulative ischemic contribution score from all coronary artery segments lying between the current location and a leaf segment, a cumulative ischemic contribution score from the non-anomalous portions of coronary artery segments lying between the current location and a leaf segment, or a cumulative ischemic contribution score from the anomalous portions of coronary artery segments lying between the current location and a leaf segment.

33. The non-transitory computer readable medium of claim 29, wherein extracting geometric features from the patient-specific coronary arterial tree geometry of the patient further comprises:
extracting a plurality of geometric measurements for one or more stenosis regions in the patient-specific coronary arterial tree geometry of the patient.

34. The non-transitory computer readable medium of claim 27, wherein the hemodynamic index is fractional flow reserve (FFR).

35. The non-transitory computer readable medium of claim 27, wherein the hemodynamic index is wall stress.

36. The non-transitory computer readable medium of claim 27, wherein computing a hemodynamic index for one or more locations of interest in the patient-specific coronary arterial tree using a trained machine-learning based surrogate model and based purely on the extracted geometric features without considering features from patient-specific physiological measurements comprises:
computing a plurality of hemodynamic indices for each of the one or more locations of interest in the patient-specific coronary arterial tree using a respective one of a plurality of trained machine-learning based surrogate models and based purely on the extracted geometric features without considering features from patient-specific physiological measurements.

* * * * *